US00PP35219P2

(12) United States Plant Patent
Vandenberg

(10) Patent No.: US PP35,219 P2
(45) Date of Patent: Jun. 13, 2023

(54) ***HIBISCUS* PLANT NAMED 'ORANGE LAVA WIND'**

(50) Latin Name: *Hibiscus rosa-sinensis*
Varietal Denomination: Orange Lava Wind

(71) Applicant: Cornelis P. Vandenberg, Fort Myers, FL (US)

(72) Inventor: Cornelis P. Vandenberg, Fort Myers, FL (US)

(73) Assignee: ARIS HORTICULTURE, INC., Barberton, OH (US)

( * ) Notice: Subject to any disclaimer, the term of this patent is extended or adjusted under 35 U.S.C. 154(b) by 9 days.

(21) Appl. No.: 17/863,371

(22) Filed: Jul. 12, 2022

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Hibiscus* plant named 'Orange Lava Wind', characterized by its semi-upright and uniformly mounded plant habit appropriate for container production; freely branching habit, dense and bushy appearance; glossy dark green-colored leaves; uniform, freely and early flowering habit; single orange-colored flowers with dark red-colored centers; good postproduction and garden performance; and resistance to Bacterial Leaf Spot.

2 Drawing Sheets

Figure 1:
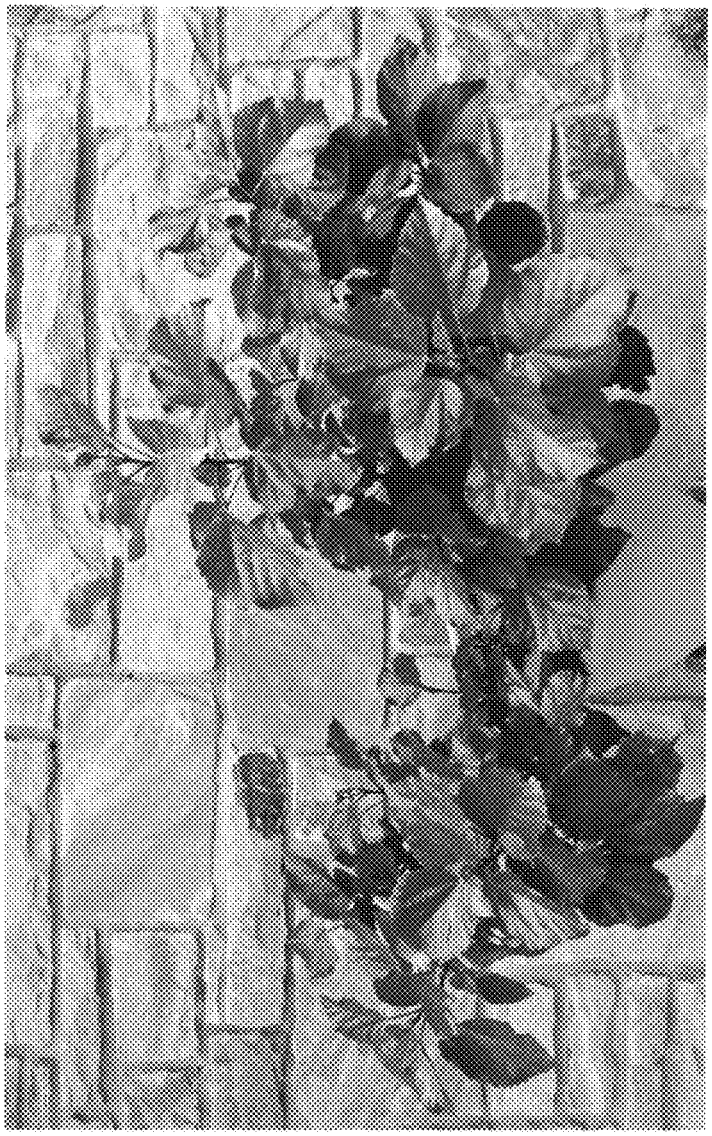

Botanical designation: *Hibiscus rosa-sinensis.*
Cultivar denomination: 'ORANGE LAVA WIND'.

BACKGROUND OF THE INVENTION

The present invention relates to a new and distinct *Hibiscus* plant, botanically known as *Hibiscus rosa-sinensis* and hereinafter referred to by the name 'Orange Lava Wind'.

The new *Hibiscus* plant is a product of a planned breeding program conducted by the Inventor in Alva, Fla. The objective of the breeding program is to create new freely-branching *Hibiscus* plants with uniform plant habit appropriate for container production, early and freely flowering habit, desirable flower color, good garden performance and resistance to Bacterial Leaf Spot.

The new *Hibiscus* plant originated from a cross-pollination made by the Inventor in Alva, Fla. in 2017 of a proprietary selection of *Hibiscus rosa-sinensis* identified as code number 3352, not patented, as the female, or seed, parent with *Hibiscus rosa-sinensis* 'Passion Wind', disclosed in U.S. Plant Pat. No. 31,124, as the male, or pollen, parent. The new *Hibiscus* plant was discovered and selected by the Inventor as a single flowering plant within the progeny of the stated cross-pollination in a controlled greenhouse environment in Alva, Fla. on Aug. 20, 2018.

Asexual reproduction of the new *Hibiscus* plant by vegetative terminal cuttings in a controlled greenhouse environment in Alva, Fla. since November, 2018 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Orange Lava Wind'. These characteristics in combination distinguish 'Orange Lava Wind' as a new and distinct *Hibiscus* plant:

1. Semi-upright and uniformly mounded plant habit appropriate for container production.
2. Freely branching habit, dense and bushy appearance.
3. Dark green-colored leaves.
4. Uniform, freely and early flowering habit.
5. Single orange-colored flowers with dark red-colored centers.
6. Good postproduction and garden performance.
7. Resistant to Bacterial Leaf Spot.

Plants of the new *Hibiscus* can be compared to plants of the female parent selection. Plants of the new *Hibiscus* differ primarily from plants of the female parent selection in the following characteristics:

1. Plants of the new *Hibiscus* have orange-colored flowers whereas plants of the female parent selection have light pink-colored flowers.
2. Plants of the new *Hibiscus* have better garden performance than plants of the female parent selection.
3. Plants of the new *Hibiscus* are more resistant to Bacterial Leaf Spot than plants of the female parent selection.

Plants of the new *Hibiscus* can be compared to plants of the male parent, 'Passion Wind'. Plants of the new *Hibiscus* differ primarily from plants of 'Passion Wind' in the following characteristics:

1. Plants of the new *Hibiscus* have orange-colored flowers whereas plants of 'Passion Wind' have red purple-colored flowers.
2. Plants of the new *Hibiscus* have better garden performance than plants of 'Passion Wind'.
3. Plants of the new *Hibiscus* are more resistant to Bacterial Leaf Spot than plants of 'Passion Wind'.

Plants of the new *Hibiscus* can be compared to plants of the *Hibiscus rosa-sinensis* 'Improved Mandarin Wind', disclosed in U.S. Plant Pat. No. 24,981. In side-by-side comparisons plants of the new *Hibiscus* differ from plants of 'Improved Mandarin Wind' in the following characteristics:

1. Plants of the new *Hibiscus* are more uniform in plant habit than plants of 'Improved Mandarin Wind'.
2. Plants of the new *Hibiscus* have better garden performance than plants of 'Improved Mandarin Wind'.
3. Plants of the new *Hibiscus* are more resistant to Bacterial Leaf Spot than plants of 'Improved Mandarin Wind'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet (FIG. 1) is a side perspective view of typical budded plants of 'Orange Lava Wind' grown in a container.

Figure 2:
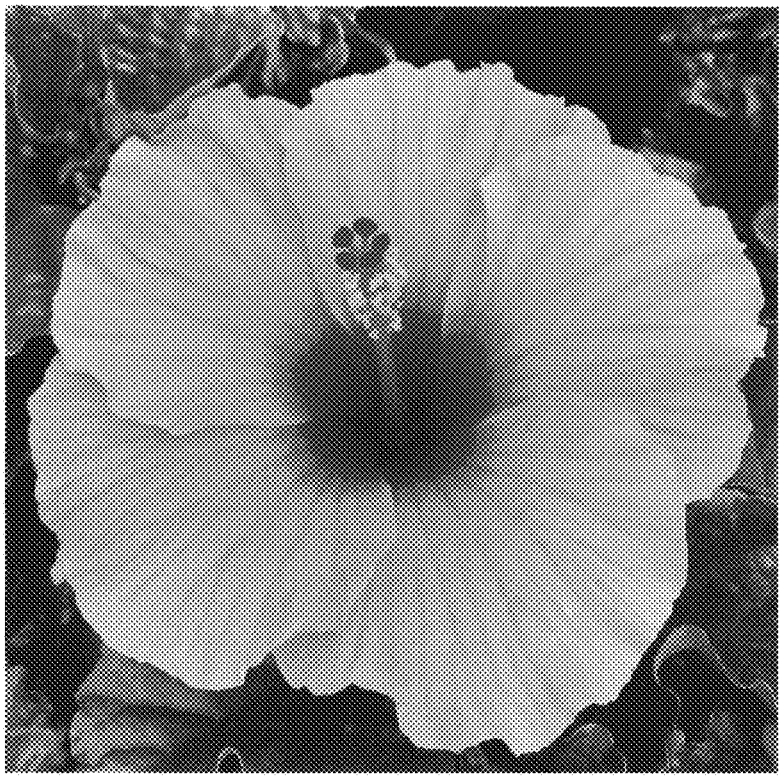

The photograph on the second sheet (FIG. 2) is a close-up view of a typical open flower of 'Orange Lava Wind'.

DETAILED BOTANICAL DESCRIPTION

The aforementioned photographs and following observations, measurements and values describe plants grown during the summer in 15-cm containers in a polyethylene-covered greenhouse in Alva, Fla. and in 25-cm containers in an outdoor nursery in Fort Worth, Tex. under cultural practices which closely approximate commercial *Hibiscus* production. During the production of the plants in Texas, day temperatures ranged from 35° C. to 40° C., night temperatures ranged from 24° C. to 35° C. and light levels ranged from 5,000 to 7,500 foot-candles. Plants were pinched two times and were ten months old when the photographs and the description were taken. In the description, color references are made to The Royal Horticultural Society Colour Chart, 2015 Edition, except where general terms of ordinary dictionary significance are used.

Botanical classification: *Hibiscus rosa-sinensis* 'Orange Lava Wind'.

Parentage:

*Female, or seed, parent.*—Proprietary selection of *Hibiscus rosa-sinensis* identified as code number 3352, not patented.

*Male or pollen parent.*—*Hibiscus rosa-sinensis* 'Passion Wind', disclosed in U.S. Plant Pat. No. 31,124.

Propagation:

*Type.*—By vegetative terminal cuttings.

*Time to initiate roots, summer and winter.*—About four to five weeks.

*Time to produce a rooted young plant, summer and winter.*—About five to six weeks.

*Root description.*—Thick, fibrous; typically white to light brown in color, actual color of the roots is dependent on substrate composition, water quality, fertilizer, substrate temperature and physiological age of roots.

*Rooting habit.*—Moderate branching; moderately dense.

Plant description:

*Plant form and growth habit.*—Perennial, evergreen, semi-upright and uniformly mounded plant habit; vigorous growth habit and rapid growth rate.

*Branching habit.*—Freely branching habit with lateral branches potentially develop at every node; pinching enhances lateral branch development; dense and bushy appearance.

*Plant height.*—About 45 cm.

*Plant diameter* (*area of spread*).—About 52 cm.

Lateral branch description:

*Length.*—About 40 cm.

*Diameter.*—About 3.5 cm.

*Internode length.*—About 1.1 cm.

*Aspect.*—Upright to somewhat outwardly spreading.

*Texture and luster, immature.*—Smooth, glabrous; matte.

*Texture and luster, mature.*—Woody and rough; matte.

*Color, immature.*—Close to 148A variably overlain with close to 187A.

*Color, mature.*—Close to N199A.

Leaf description:

*Arrangement.*—Alternate, single; numerous; symmetrical.

*Length.*—About 9.1 cm.

*Width.*—About 9.25 cm.

*Shape.*—Broadly ovate.

*Apex.*—Acute.

*Base.*—Truncate.

*Margin.*—Crenate.

*Texture and luster, upper surface.*—Smooth, glabrous; semi-glossy.

*Texture and luster, lower surface.*—Slightly rough, glabrous; matte.

*Venation pattern.*—Pinnate; arcuate.

*Color.*—Developing leaves, upper surface: Darker green than 146A. Developing leaves, lower surface: Close to 146B. Fully expanded leaves, upper surface: Darker green than NN137A; midvein, close to 146A and lateral venation, close to NN137A. Fully expanded leaves, lower surface: Close to N137B; venation, close to 146A.

*Petioles.*—Length: About 3.7 cm. Diameter: About 2 mm. Texture and luster, upper surface: Smooth, glabrous; matte. Texture and luster, lower surface: Slightly rough, glabrous; matte. Color, upper and lower surfaces: Close to 146A variably overlain with close to 187A.

Flower description:

*Flower arrangement and flowering habit.*—Rounded single flowers arranged at terminal leaf axils; uniform and freely flowering habit with about two to three flowers per terminal; flowers face mostly upright to slightly outwardly.

*Natural flowering season.*—Plants of the new *Hibiscus* flower naturally during the spring and summer or during periods of warm weather; plants flower year-round in the greenhouse.

*Flower longevity.*—Depending on temperature and water status, flowers typically last about two to three days on the plant; flowers persistent.

*Flower diameter.*—About 10.25 cm.

*Flower length* (*height*).—About 8.5 cm.

*Flower buds.*—Resistance to abscission during shipping: Plants of the new *Hibiscus* have been observed to resist flower bud drop during shipping. Length: About 1.5 cm. Diameter: About 9 mm. Shape: Ovoid. Texture and luster: Smooth, glabrous; slightly glossy. Color: More green than 137A.

*Petals.*—Arrangement: Corolla consists of a single whorl of five petals that are fused at base; petals imbricate. Length: About 7.25 cm. Width: About 6.5 cm. Shape: Roughly spatulate. Apex: Rounded; undulate. Base: Attenuate. Margin: Entire; undulate. Texture and luster, upper surface: Smooth, glabrous; velvety; slightly glossy. Texture and luster, lower surface: Glabrous; veins prominent; semi-glossy. Color: When opening and fully opened, upper surface: Close to N25A to N25B; towards the throat, close to 53C and throat, close to 53A. When opening and fully opened, lower surface: Close to 25B to 25C.

*Sepals.*—Appearance: Five sepals in a single whorl fused into a tubular star-shaped calyx. Length: About 2.5 cm. Width: About 1.2 cm. Shape: Lanceolate. Apex: Sharply acute. Margin: Entire. Texture and luster, upper surface: Smooth, glabrous; glossy. Texture and luster, lower surface: Smooth, glabrous; matte. Color, upper surface: Close to 146B to 146C. Color, lower surface: Darker green than 146A.

*Epicalyx.*—Quantity and arrangement: About six to seven in a single whorl fused at base. Length: About 1.5 cm. Width: About 5 mm. Shape: Lanceolate. Apex: Sharply acute. Margin: Entire. Texture and luster, upper and lower surfaces: Smooth, glabrous; matte. Color, upper surface: Close to 146A. Color, lower surface: More green than 147A.

*Peduncles.*—Length: About 2.5 cm to 3.5 cm. Diameter: About 2.25 mm. Aspect: Upright to slightly outwardly. Strength: Strong, flexible. Texture and luster: Smooth, glabrous; slightly glossy. Color: Close to 144A; proximally, tinged with close to 187A.

*Reproductive organs.*—Androecium: Stamen number: Numerous, about 35 per flower. Filament length: About 5 mm. Filament color: Close to 25A to 25B. Anther shape: Oblong. Anther length: About 1.75 mm. Anther color: Close to 25A. Amount of pollen: Sparse to moderate. Pollen color: Close to N25B. Gynoecium: Pistil number: One per flower. Pistil length: About 7.6 cm. Style length: About 6.4 cm. Style texture and luster: Smooth, glabrous; waxy; glossy. Style color: Close to 46A. Stigma appearance: Five-parted, rounded. Stigma color: Close to 53A. Ovary color: Close to 11C to 11D.

*Seeds and fruits.*—To date, seed and fruit production has not been observed on plants of the new *Hibiscus*.

Garden performance: Plants of the new *Hibiscus* have been observed to have good garden performance and to tolerate wind, rain and temperatures ranging from about 1° C. to about 40° C.

Pathogen & pest resistance: Plants of the new *Hibiscus* have been observed to be resistant to Bacterial Leaf Spot (*Pseudomonas cichorii*). To date, plants of the new *Hibiscus* grown under Florida production conditions have not been shown to be resistant to pests and other pathogens common to *Hibiscus* plants.

It is claimed:

1. A new and distinct *Hibiscus* plant named 'Orange Lava Wind' as illustrated and described.

* * * * *